(12) United States Patent
Hassett et al.

(10) Patent No.: US 6,251,109 B1
(45) Date of Patent: Jun. 26, 2001

(54) PROCESS AND DEVICE FOR THE TREATMENT OF ATRIAL ARRHYTHMIA

(75) Inventors: James A. Hassett, Bloomington, MN (US); John F. Swartz, Afton, OK (US); Michael C. Bednarek, Buffalo, MN (US)

(73) Assignee: Daig Corporation, Minnetonka, MN (US)

(*) Notice: Subject to any disclaimer, the term of this patent is extended or adjusted under 35 U.S.C. 154(b) by 0 days.

(21) Appl. No.: 09/233,337

(22) Filed: Jan. 20, 1999

Related U.S. Application Data

(63) Continuation-in-part of application No. 08/883,668, filed on Jun. 27, 1997, now Pat. No. 5,938,660.

(51) Int. Cl.$^7$ .................................................. A61B 18/18
(52) U.S. Cl. ........................ 606/45; 606/49; 607/101; 607/122
(58) Field of Search .............................. 604/93, 100, 21; 606/41, 45, 49, 198; 607/96, 98, 101, 102, 116, 119, 122

(56) References Cited

U.S. PATENT DOCUMENTS

| | | |
|---|---|---|
| 4,445,892 | 5/1984 | Hussein et al. . |
| 4,641,649 | 2/1987 | Walinsky et al. . |
| 4,911,163 | 3/1990 | Fina . |
| 4,945,912 | 8/1990 | Langberg . |
| 5,002,532 | 3/1991 | Gaiser et al. . |
| 5,103,804 | * 4/1992 | Abele et al. . |
| 5,106,360 | * 4/1992 | Ishiwara et al. ............... 600/2 |
| 5,209,229 | 5/1993 | Gilli . |
| 5,228,442 | 7/1993 | Imran . |
| 5,231,995 | 8/1993 | Desai . |
| 5,242,441 | 9/1993 | Avitall . |
| 5,246,438 | 9/1993 | Langberg . |
| 5,256,141 | 10/1993 | Gencheff et al. . |
| 5,263,493 | 11/1993 | Avitall . |
| 5,271,392 | 12/1993 | Ferek-Petric . |
| 5,281,213 | 1/1994 | Milder et al. . |
| 5,281,217 | 1/1994 | Edwards et al. . |
| 5,281,218 | 1/1994 | Imran . |
| 5,282,836 | 2/1994 | Kreyenhagen et al. . |
| 5,293,868 | 3/1994 | Nardella . |
| 5,366,490 | 11/1994 | Edwards et al. . |

(List continued on next page.)

FOREIGN PATENT DOCUMENTS

WO 96/00042   1/1996   (WO) .

OTHER PUBLICATIONS

Cox, J.L. *Electrophysiology, Pacing and Arrhythmia*, "Operations for Atrial Fibrillation", Clin. Cardiol. vol. 14, pp. 827–834 (1991).
Falk, R.H., et al., *Atrial Fibrillation Mechanisms and Management*, pp. 359–374 (1992).
Horowitz, L.N. *Current Management of Arrhythmias*, pp. 373–375 (1991).
Martin, D., et al., *Atrial Fibrillation*, pp. 42–59 (1994).
Singer, I., et al., "Catheter Ablation for Arrhythmias" *Clinical Manual of Electrophysiology*, pp. 421–431 (1993).

Primary Examiner—John P. Leubecker
Assistant Examiner—Roy Gibson
(74) Attorney, Agent, or Firm—Scott R. Cox

(57) ABSTRACT

A process for the treatment of atrial arrhythmia by use of ablation procedures including circumferential ablation of vessels, particularly pulmonary veins, associated with the left atrium of the heart. Also medical devices for such process including a pair of balloons secured to a catheter with one balloon located within the other balloon and an ablation catheter located within one of the balloons, which devices are used for the formation of a circumferential ablation lesion in the pulmonary vein.

22 Claims, 10 Drawing Sheets

U.S. PATENT DOCUMENTS

| | | |
|---|---|---|
| 5,427,119 | 6/1995 | Swartz et al. . |
| 5,462,529 | 10/1995 | Simpson et al. . |
| 5,468,239 | 11/1995 | Tanner et al. . |
| 5,484,412 | 1/1996 | Pierpont . |
| 5,497,774 | 3/1996 | Swartz et al. . |
| 5,536,247 * | 7/1996 | Thornton ................................ 604/49 |
| 5,564,440 | 10/1996 | Swartz et al. . |
| 5,575,766 | 11/1996 | Swartz et al. . |
| 5,588,961 | 12/1996 | Leone et al. . |
| 5,599,307 | 2/1997 | Bacher et al. . |
| 5,628,316 | 5/1997 | Swartz et al. . |
| 5,640,955 | 6/1997 | Ockuly et al. . |
| 5,681,308 | 10/1997 | Edwards et al. . |
| 5,785,706 | 7/1998 | Bednarek . |
| 5,792,105 | 8/1998 | Lin et al. . |
| 5,800,482 | 9/1998 | Pomeranz et al. . |
| 5,807,306 * | 9/1998 | Shapland et al. ...................... 604/21 |
| 5,971,983 * | 10/1999 | Lesh ...................................... 606/41 |

* cited by examiner

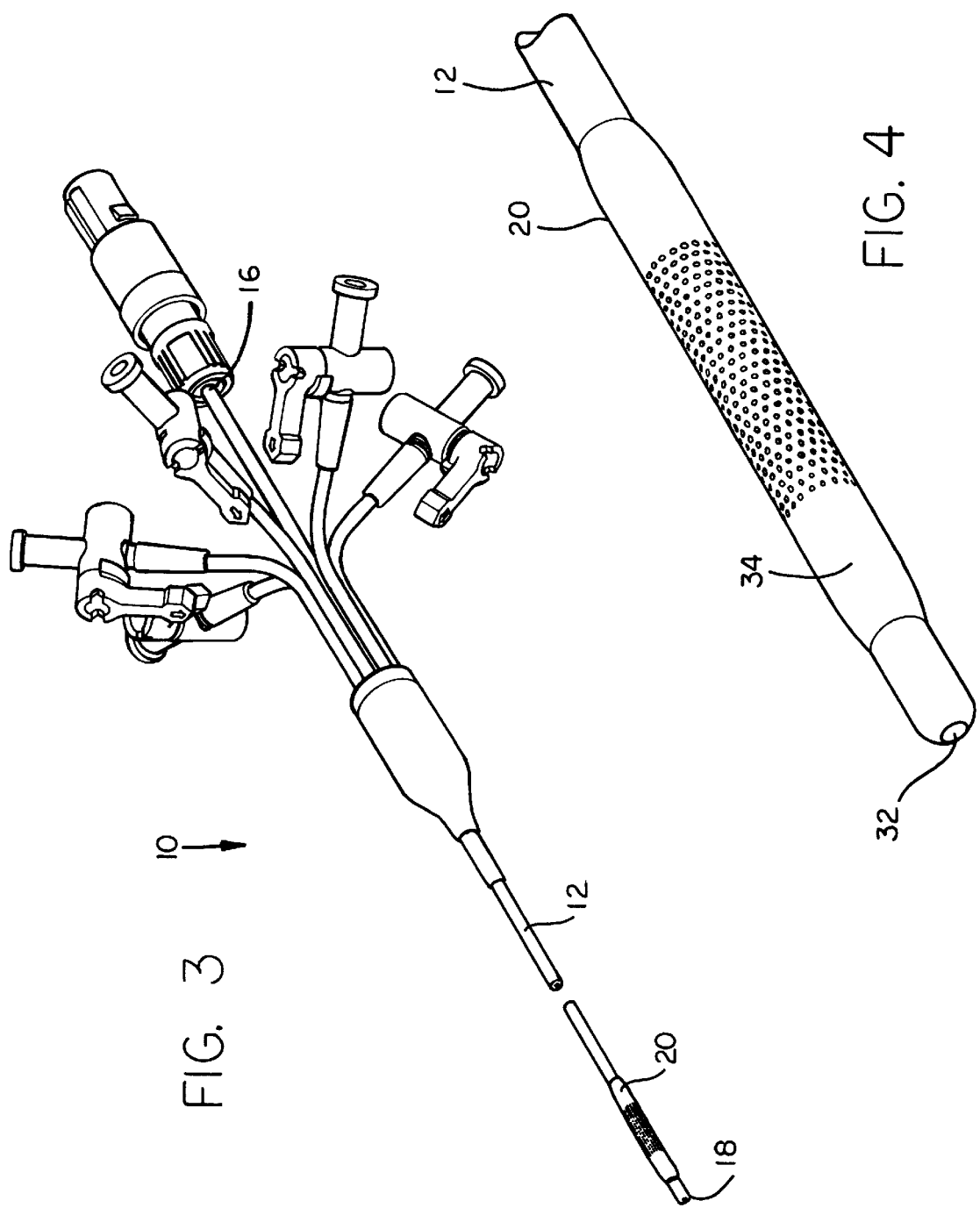

PROCESS AND DEVICE FOR THE TREATMENT OF ATRIAL ARRHYTHMIA

CROSS REFERENCE TO RELATED APPLICATION

This application is a continuation-in-part application based on application Ser. No. 08/883,668, filed Jun. 27, 1997, now U.S. Pat. No. 5,938,660.

BACKGROUND OF INVENTION

This invention relates to medical devices and processes useful for the treatment of atrial arrhythmia. In particular, it relates to a preferred process and medical device used for ablation procedures in vessels of the human body, namely the pulmonary veins.

Introducers and catheters have been in use for medical procedures for many years. For example, one procedure utilizes a catheter to convey an electrical stimulus to a selected location within the human body. Another procedure utilizes a catheter to monitor activity in various locations in the body for diagnostic tests. Thus, catheters may examine, diagnose and treat while positioned at specific locations within the body which are otherwise inaccessible without more invasive procedures. In use, catheters may be inserted into a major vein or artery which is near the body surface. These catheters are then guided to a specific location for examination, diagnosis and treatment by manipulating the catheter through the artery or vein of the human body, frequently with the assistance of other medical devices, such as introducers or guidewires.

One common medical procedure utilizing specialized catheters is the treatment of vessels located within the human body, frequently vessels associated with the human heart. Those procedures, most notably angioplasty procedures, utilize a catheter which often contains an inflatable balloon secured to the catheter. In some of these medical procedures, the catheter contains a pair of inflatable balloons used to limit the portion of the vessel that is treated or to assure that the catheter remains at a fixed location within the vessel throughout the medical procedure or to assist in the performance of the medical procedure.

Multiple balloon catheters are utilized throughout the body. For example, U.S. Pat. No. 5,468,239 discloses a device for circumferential laser burning of tissue in a urethral canal. This device utilizes a pair of cuffs or balloons (60) with a laser probe (12) located between those balloons. U.S. Pat. No. 5,588,961 discloses an infusion catheter for delivery of medication to a vessel and contains a pair of balloons (16, 17) and an electrode (35) secured to the catheter. Ports are provided in the catheter to introduce the medication into the space between the two balloons within the vessel. Energy may also be introduced into the electrode to encourage the movement of the medication away from the catheter toward the walls of the vessel. U.S. Pat. No. 5,256,141 discloses a pair of balloons (14, 18) with an electrode secured to a catheter to apply a controlled electric charge to material introduced into the space in the vessel between the two balloons.

Biological material may also be introduced into this space for medical treatment of the vessel. U.S. Pat. No. 5,366,490 discloses a pair of balloons (30, 32) secured to a catheter and a stylette (36). Radio frequency energy is supplied to the catheter to destroy tissue. U.S. Pat. No. 5,599,307 discloses a pair of balloons (41, 42) secured to a catheter designed to occlude a vessel. U.S. Pat. No. 5,002,532 discloses a pair of balloons (21, 22) secured to a catheter (12) for use in a dilation procedure within a vessel, whereby the two balloons may be inflated to different extents. U.S. Pat. No. 5,792,105 discloses a multichannel balloon catheter for delivering fluids which utilizes an inner and an outer balloons. See also U.S. Pat. No. 4,445,892.

In addition to the use of multiple balloons on a single catheter for medical procedures, U.S. Pat. No. 5,462,529 discloses a medical device containing a pair of catheters (12, 28), each containing a balloon (20, 48) secured at or near its distal end, which device is utilized to perform a medical procedure within a vessel. U.S. Pat. No. 5,484,412 also discloses a pair of catheters (18, 22) utilized to perform a medical procedure within a vessel, each containing an inflatable balloon (36, 38). U.S. Pat. No. 4,911,163 discloses a pair of balloons (2, 8) secured to a pair of catheters (1, 7) for introduction of medicine or diagnostic fluids into the space between the two balloons.

Atrial fibrillation is the most common sustained heart arrhythmia. It is estimated to occur in upwards of 0.4 percent of the adult population and perhaps as many as 10 percent of the population who are 60 years or older. Cox, J. L., et al., *Electrophysiology, Pacing and Arrhythmia*, "Operations for Atrial Fibrillation," Clin. Cardiol. 14, 827–834 (1991).

Atrial arrhythmia may be transient or persistent. While most atrial arrhythmia occur in individuals having other forms of underlying heart disease, some atrial arrhythmia occur independently. While atrial arrhythmia do not directly cause death as frequently as ventricular arrhythmia, they increase the risk factors for a number of other diseases such as systemic and cerebral embolism and may cause a number of additional medical problems.

In the treatment of atrial arrhythmia, antiarrhythmic drugs sometimes provide relief. Other treatments for atrial arrhythmia or fibrillation involve the use of an implanted atrial defibrillator or cardioversion. See, for example, U.S. Pat. Nos. 5,282,836, 5,271,392 and 5,209,229 and Martin, D., et al., *Atrial Fibrillation*, pgs. 42–59 (1994).

Certain patients with symptomatic or life threatening atrial arrhythmia, however, cannot be adequately treated by drugs or these types of medical devices. Other forms of aggressive treatment are sometimes mandated, which have in the past included surgery. For example, a surgical procedure for the treatment of atrial arrhythmia known as the "Maze" procedure is discussed in Cox, J. L. et al., *Electrophysiology, Pacing and Arrhythmia*, "Operations for Atrial Fibrillation," Clin. Cardiol. Vol. 14, pgs. 827–834 (1991).

Another procedure increasingly used within the last 10 to 15 years for the treatment of certain types of cardiac arrhythmia involves ablation of cardiac tissue. For example, this procedure has been commonly used to interrupt or modify existing conduction pathways associated with arrhythmia within the heart. The particular area for ablation depends on the type of underlying arrhythmia. The use of radio frequency catheter ablation for the treatment of paroxysmal atrial fibrillation is disclosed in Haissaguerre, M., et al., "Right and Left Atrial Radiofrequency Catheter Therapy of Paroxysmal Atrial Fibrillation" *J. Cardiovascular Electrophysiology*, V.7, pgs. 1132–1144 (December 1996). Ablation procedures have also been used for the treatment of atrioventricular (AV) nodal reentrant tachycardia. With this condition, ablation of the fast or slow AV nodal pathways has become an accepted treatment. Singer, I., et al., "Catheter Ablation for Arrhythmias" *Clinical Manual of Electrophysiology*, pgs. 421–431 (1993); Falk, R. H., et al., *Atrial Fibrillation Mechanisms in Management*, pgs.

359–374 (1992); Horowitz, L. N., *Current Management of Arrhythmias*, pgs. 373–378 (1991); and Martin, D., et al., *Atrial Fibrillation*, pgs. 42–59 (1994). In addition, the use of ablation catheters for ablating locations within the heart has been disclosed, for example in U.S. Pat. Nos. 4,641,649, 5,263,493, 5,231,995, 5,228,442 and 5,281,217.

The sources of energy used for catheter ablation vary. Initially, high voltage, direct current (DC) ablation techniques were commonly used. However, because of problems associated with the use of DC current, radio frequency (Rf) energy has become the preferred source of energy for ablation procedures. The use of Rf energy for ablation has been disclosed, for example, in U.S. Pat. Nos. 4,945,912, 5,209,229, 5,281,218, 5,242,441, 5,246,438, 5,281,213 and 5,293,868. Other energy sources which are being used currently or are being considered for ablation of heart tissue include laser, ultrasound, microwave and fulgutronization.

Ablation of a precise location within the heart requires the precise placement of the ablation catheter within the heart. Precise positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

A process for the mapping and treatment of atrial arrhythmia using ablation catheters guided to a specific location by shaped, guiding introducers is disclosed in U.S. Pat. Nos. 5,427,119, 5,497,774, 5,575,766, 5,564,440, 5,628,316 and 5,640,955. In particular, a process for the ablation of defined tracks within the left and/or right atrium as an element of the treatment of atrial fibrillation is disclosed in U.S. Pat. No. 5,575,766.

The mechanism for initiation of some forms of atrial arrhythmia, such as atrial premature contractions, is not well understood. As a result, ablation procedures in the heart have focused on the formation of lesions within the chambers of the heart at selected locations which either prevent the passage of electrical signals associated with atrial premature contractions or prevent the formation of improper electrical pathways within the heart, which can result in atrial arrhythmia.

It has been surprisingly discovered that one source for these atrial premature contractions originates within vessels associated with the heart, in particular the pulmonary veins. Once these atrial premature contractions form in the pulmonary veins, they are periodically conducted into the left atrium. When the atrial premature contractions enter the left atrium, they can initiate or continue an episode of atrial fibrillation.

Invasive treatment of atrial fibrillation in the past around the pulmonary veins has been limited to the formation of lesions in the left atrium created by an invasive surgical procedure, such as is disclosed by Cox, J. L., et al., Electrophysiology, Pacing and Arrhythmia, "Operations for Atrial Fibrillation" *Clin. Cardiol.* Vol. 14, pgs. 827–834 (1991). In addition, the use of precurved guiding introducers to guide ablation catheters to appropriate locations in the left atrium for use in the formation of lesions around the pulmonary veins has been disclosed in U.S. Pat. No. 5,575,766.

While these procedures have been successful in some patients, other patients require additional treatment as the treatments previously disclosed have not been completely successful in the elimination of the atrial fibrillation. In addition, these ablation procedures can be very time consuming, requiring as long as 10–15 hours.

It is therefore an aspect of this invention to disclose a medical device useful in the treatment of atrial arrhythmia, particularly atrial fibrillation.

It is an additional aspect of this invention to disclose a medical device useful for the formation of ablation lesions in vessels in the body.

It is a still further aspect of this invention to disclose a medical device containing a pair of inflatable balloons, one located inside of the other, and an ablation electrode, which components are utilized to form a circumferential ablation lesion for the treatment of atrial arrhythmia, particularly atrial premature contractions.

It is a still further aspect of this invention to disclose a process for the formation of circumferential ablation lesions in vessels in the human body.

It is a still further aspect of this invention to disclose a process for ablation of tissue located within the pulmonary veins, or on the os of the pulmonary veins.

It is a still further aspect of this invention to disclose a process for the formation of circumferential lesions in the pulmonary veins, or on the os of the pulmonary veins.

It is a still further aspect of this invention to disclose medical procedures for the production of circumferential ablation lesions within vessels of the heart, or on the os of those vessels, for the treatment of atrial fibrillation.

It is a still further aspect of this invention to disclose a process for the formation of ablation lesions within a vessel of the heart, or on the os of that vessel, using Rf energy.

These and other aspects of the invention are disclosed by the processes for the treatment of atrial arrhythmia and the design of the medical products for use with those processes.

SUMMARY OF INVENTION

The present invention is an ablation catheter useful for ablation procedures within a vessel of a human, or on the os of that vessel, particularly a pulmonary vein. A first and a second balloon are secured to the catheter, with the second balloon secured to the catheter and located inside the first balloon. The balloons, when inflated, seal the vessel and prevent substantially the flow of blood through the vessel around these balloons. An introduction system is also included as an element of the ablation catheter to introduce a conductive media to the space within the first and second balloons when inflated. The first balloon contains a plurality of balloon openings in its outside surface through which the conductive media is expelled to contact the tissue of the vessel. An ablating system is also included as an element of the ablation catheter, which system is secured to the catheter at a location within the first, outer balloon, but outside of the second, inner balloon. The ablating system includes one or more Rf energy ablation electrodes, which may be in the form of a coil electrode or a ring electrode. The conductive media conducts the ablating energy from the ablating system out through the balloon openings in that first balloon to contact the tissue located in the vessel, or on the Os of the vessel, adjacent to the balloon openings to form a circumferential ablation lesion in the vessel or on the os of the vessel.

Alternatively, the present invention is a medical device for ablation within a vessel of a human, or on the os of that vessel, and includes the catheter system discussed above used in conjunction with a shaped guiding introducer with a proximal and distal end and a lumen passing from its proximal to its distal end. The shaped introducer guides the ablation catheter to the desired location in the vessel, or on the os of that vessel, to perform the ablation procedure.

Also disclosed is a process for the ablation of tissue within a vessel of a human, particularly a pulmonary vein, which includes introducing an ablation catheter containing a first, and a second balloon and an electrode into the vessel, or on the os of the vessel, wherein the second balloon is located within the first balloon, sealing the vessel to prevent substantially the flow of blood through the vessel using the first and second balloons, passing conductive media from within the first balloon through a plurality of balloon openings in the surface of the first balloon and conducting energy from the ablation electrode by use of the conductive media to contact the tissue within the vessel, or the os of the vessels, resulting in the formation of a circumferential ablation lesion.

BRIEF DESCRIPTION OF THE DRAWINGS

FIG. 3 is a perspective view of the ablation catheter of the present invention with the balloons not inflated.

FIG. 4 is a perspective view of a distal portion of the ablation catheter of FIG. 3 with the balloons not inflated.

DETAILED DESCRIPTION OF THE PREFERRED EMBODIMENT

Figure 1:
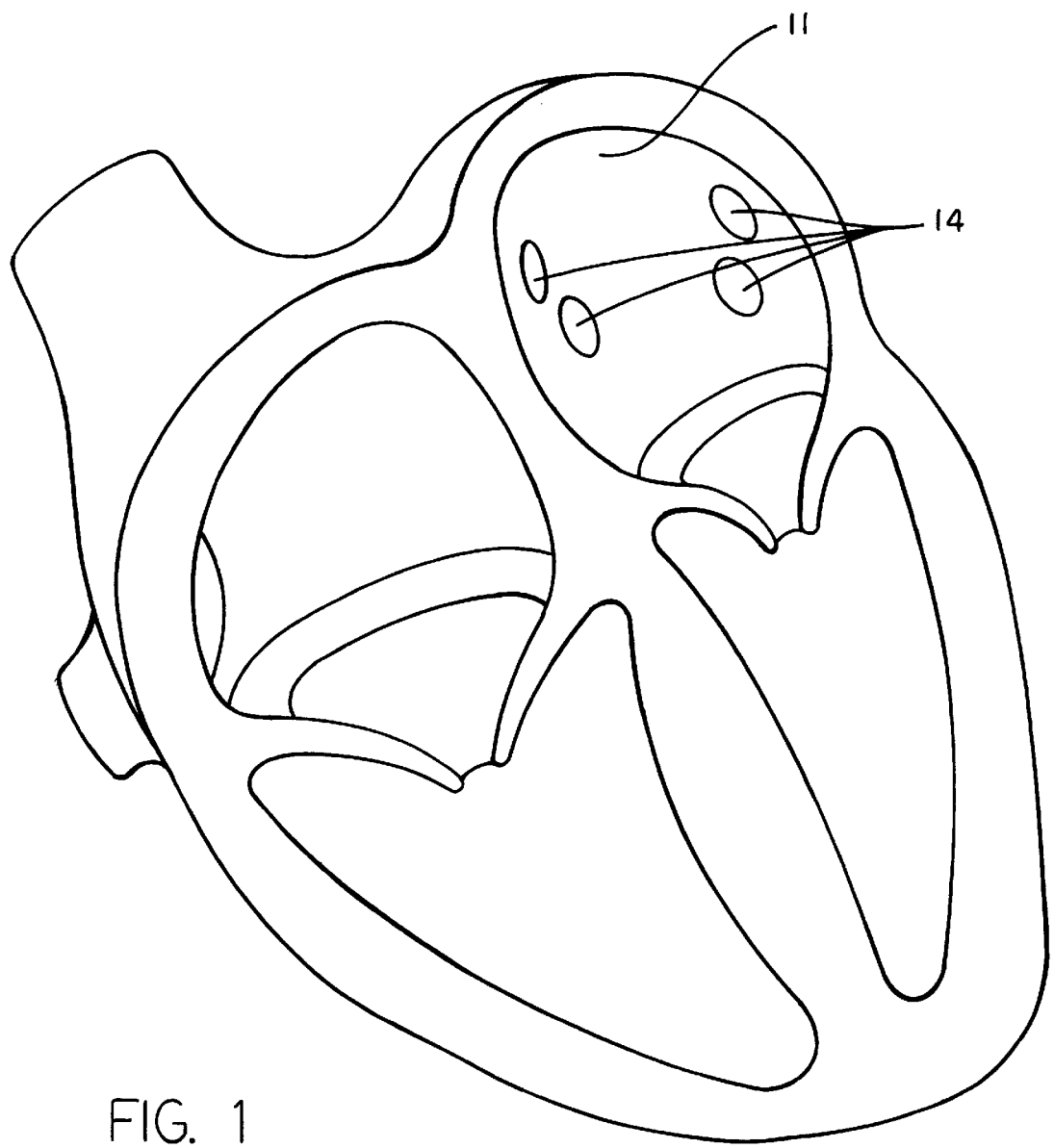
FIG. 1 is a cut away view of the heart showing the left atrium and the four pulmonary veins.

A typical human heart includes a right ventricle, a right atrium, a left ventricle and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle. On the inner wall of the right atrium where it is connected with the left atrium is a thin walled, recessed portion, the fossa ovalis. A drawing of a human heart with the left atrium (11) and the openings (os) into the respective pulmonary veins (14) is shown in FIG. 1.

In a normal heart, contraction and relaxation of the heart muscle (myocardium) takes place in an organized fashion as electrochemical signals pass sequentially through the myocardium from the sinoatrial (SA) node to the atrioventricular (AV) node and then along a well defined route which includes the His-Purkinje system into the left and right ventricles. Initial electrical impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atria which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including: (1) an irregular heart rate which causes the patient discomfort and anxiety, (2) loss of synchronous atrioventricular contractions which compromises cardiac hemodynamics resulting in varying levels of congestive heart failure, and (3) stasis of blood flow, which increases the vulnerability of the patient to thromboembolism.

Efforts to alleviate these problems have included significant usage of pharmacological treatments and occasionally surgical procedures. It has been discovered that similar success can be achieved without invasive surgery by ablation procedures performed within the atria as disclosed in U.S. Pat. No. 5,575,766. To accomplish this non-invasive procedure successfully, the ablation catheter must be positioned at pre-determined locations within the right and left atria to ablate predetermined tracks, thus forming a natural barrier to the formation of reentry circuits.

The specific pathological cause for atrial fibrillation is not well understood. It has been surprisingly discovered that one source for atrial premature contractions which may cause atrial fibrillation, particularly paroxysmal atrial fibrillation, originates in the pulmonary veins associated with the left atrium of the heart.

Figure 2:
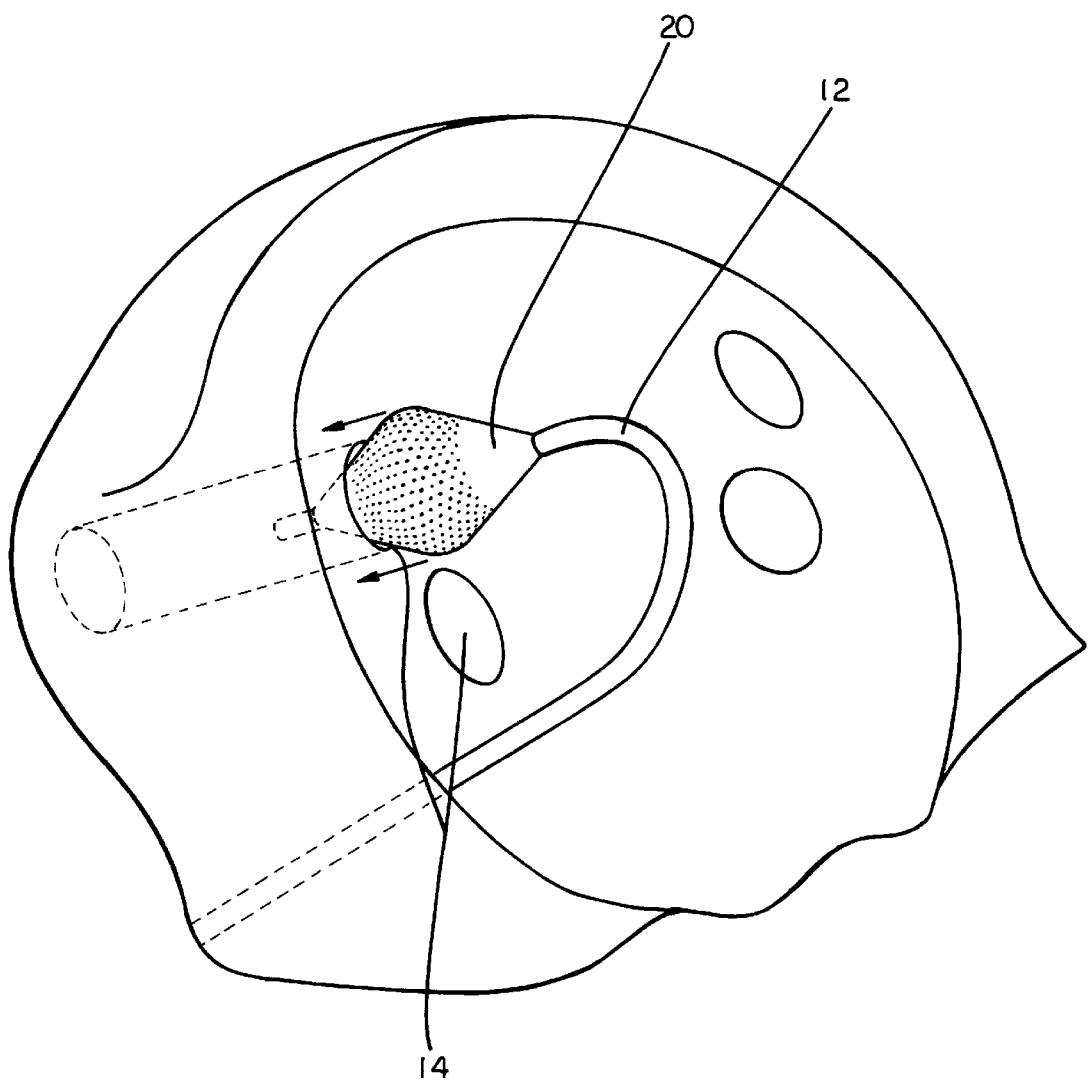
FIG. 2 is a cut away view of the left atrium showing the ablation catheter of the present invention being introduced into one of the pulmonary veins.
Figure 2A:
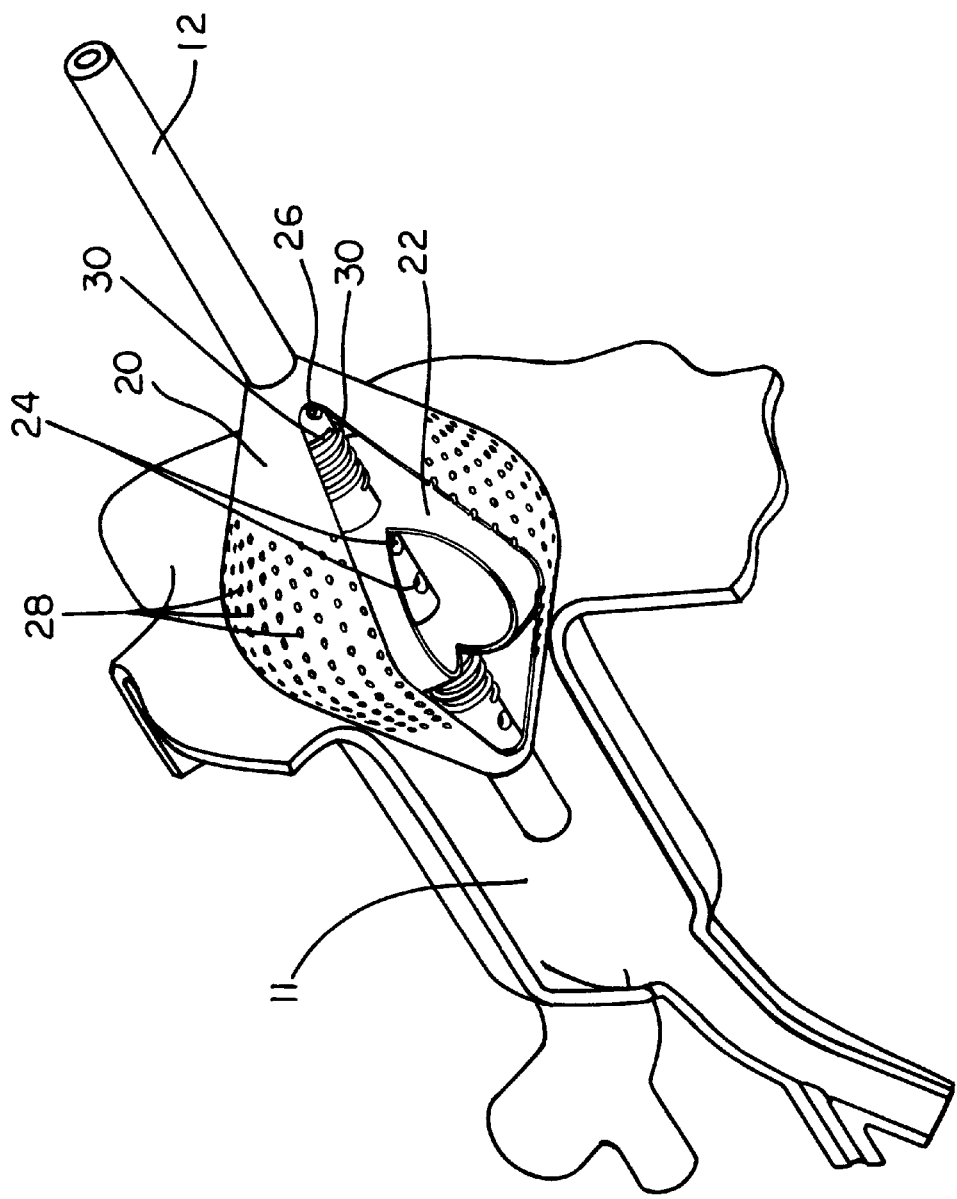
FIG. 2A is a cut away view of the ablation catheter of the present invention being introduced into one of the pulmonary veins.

In order to understand the structure of the medical devices of the invention, the medical procedure for their use within the heart must first be understood. In use, the medical device (10) of the present invention is advanced into the left atrium (11) and is then introduced into the appropriate pulmonary vein (14) or os of that pulmonary vein as shown in FIGS. 2 and 2A. (It is understood that ablation procedures may be necessary in more than one of the pulmonary veins. However, for purposes of discussion of the invention, the process will be limited to medical procedures performed in a single pulmonary vein.) Once in place, the ablation catheter (12) creates a lesion which electrically isolates the source of the atrial premature contraction in the pulmonary vein (14) from connection with the left atrium (11).

The pulmonary veins (14) are generally tubular in structure, increasing in size as they open into the left atrium (11). It has been discovered that the conduction of atrial premature contraction through a pulmonary vein (14) into the left atrium (11) can be completely halted by formation of a circumferential ablation lesion around the pulmonary vein (14), or in some circumstances around the os of the pulmonary vein, at a location proximal from the source of the atrial premature contraction. Merely ablating a single point on the surface of the pulmonary vein (14), which is perceived to be the source of the premature atrial contraction, may not be sufficient to isolate the source of the atrial premature contraction from the left atrium (11).

It is also important that the medical practitioner be able to monitor the electrical activity of the pulmonary vein (14) both before and after the ablation procedure is complete to assure that the source of atrial premature contraction has been successfully isolated from the left atrium (11).

Conventional procedures for ablation within the heart generally utilize either a conventional tip electrode or one or more ring electrodes on an ablation catheter. To effectively and efficiently ablate tissue, these electrodes are relatively small in diameter, usually in the range of about 5 French to about 8 French (1 French equals one-third millimeter (0.039 in.)). Because the diameter of a pulmonary vein (14) may be as large as about 20 millimeters (0.79 in.), it is impractical to use a conventional ablation electrode on a conventional ablation catheter to form the circumferential lesion around the inside of a pulmonary vein (14).

The steps of the process in one embodiment of the present invention for the formation of a circumferential ablation lesion within a pulmonary vein (14) include introducing into a pulmonary vein (14), or into the Os of the pulmonary vein, an ablation catheter (12) containing a pair of balloons (20, 22), one located within the other, to prevent the flow of blood through the pulmonary vein (14) as shown in FIGS. 2 and 2A. The ablation catheter (12) also includes an ablating system for ablating tissue, which system is secured to the catheter (12) but located inside the pair of balloons (20, 22). Finally the tissue within the pulmonary vein (14), or the os of the pulmonary vein, is ablated at a location proximal to the source of the atrial premature contraction to form a circumferential lesion.

Figure 5:
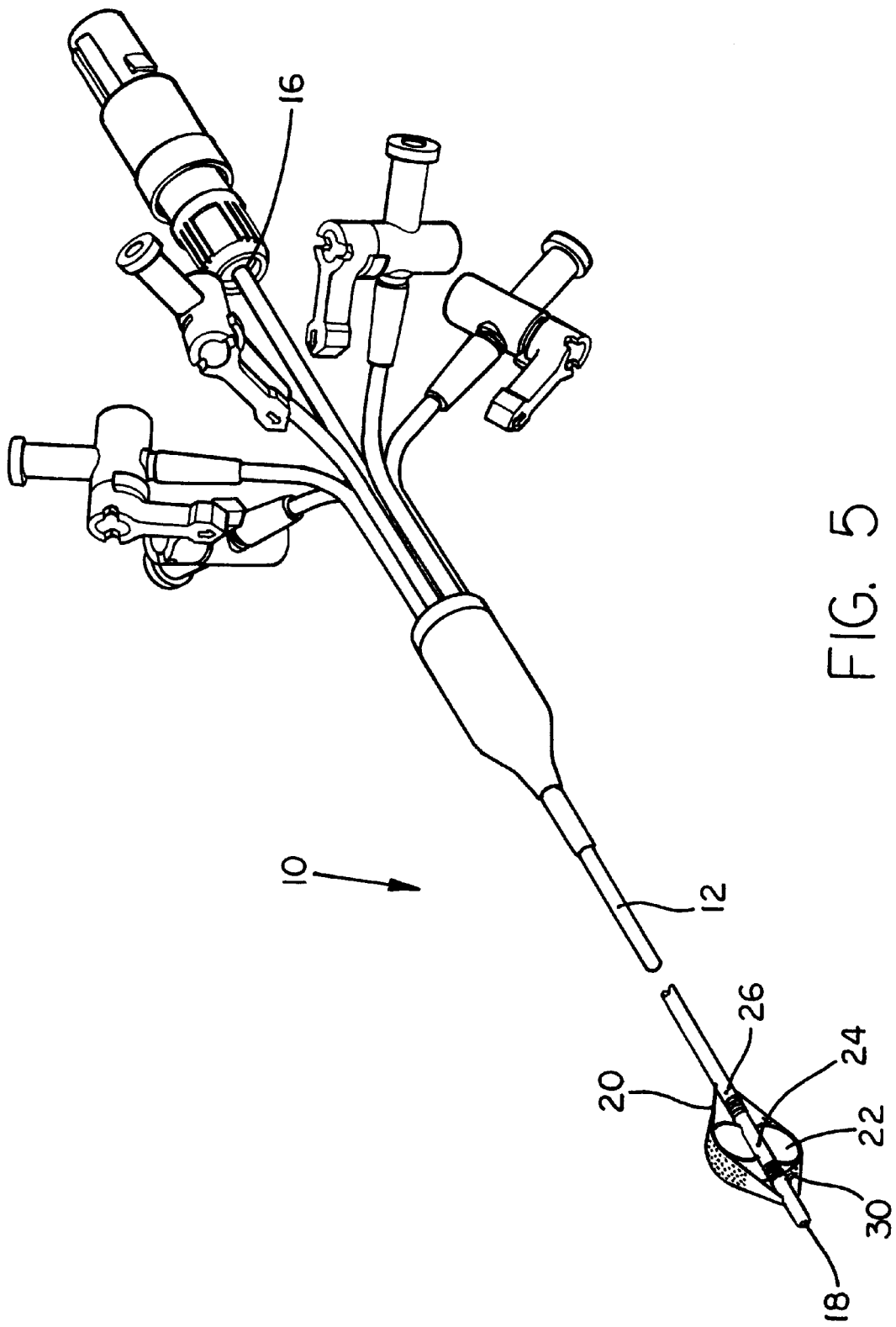
FIG. 5 is a cut away, perspective view of the ablation catheter of FIG. 3 with the balloons inflated.

In a first preferred embodiment the medical device (10) includes the catheter (12) onto which the first balloon (20) and the second balloon (22) are secured as shown in FIGS. 2–9. The catheter (12) of the first embodiment of the present invention contains a proximal end (16) and a distal end (18) as shown in FIGS. 3 and 5. The composition of the catheter (12) is conventional and should be sufficiently pliable to permit the catheter (12) to be advanced through the vasculature into the heart, across the chambers of the heart and ultimately into the pulmonary vein (14). While the distal portion of the catheter (12) may be more pliable than the remaining portion of the catheter (12), the pliability of the catheter (12) may also be consistent throughout the length of the catheter (12). An increase in pliability can be achieved through conventional procedures well known in the industry. To assist in the advancement of the catheter (12) through the vasculature and through the chambers of the heart, the main portion of the catheter (12) may be stiffer and less pliable than the distal portion of the catheter (12). In one embodiment, this main portion can be formed of any conventional catheter material having shape memory or permitting distortion from and subsequent substantial return to its desired shape. This main portion may also be reinforced, for example, by use of a reinforcing braid or other such suitable strand material having high temporal strength. The enhanced pliability of the distal portion of the catheter can be achieved by a number of methods well known in the industry, including the use of a fused flexible tip catheter or a soft tipped catheter comprised of the same or similar materials with similar performance characteristics as are present in the reinforced portion of the catheter (12). In addition, a more pliable distal portion of the catheter (12) can be created through modifications made in the catheter (12) such as by additional drawing of the catheter body to reduce the thickness of the walls, thus achieving enhanced pliability.

The overall length of the catheter (12) should be about 50 to about 150 cm. (20 to about 60 in.)

Figure 6:
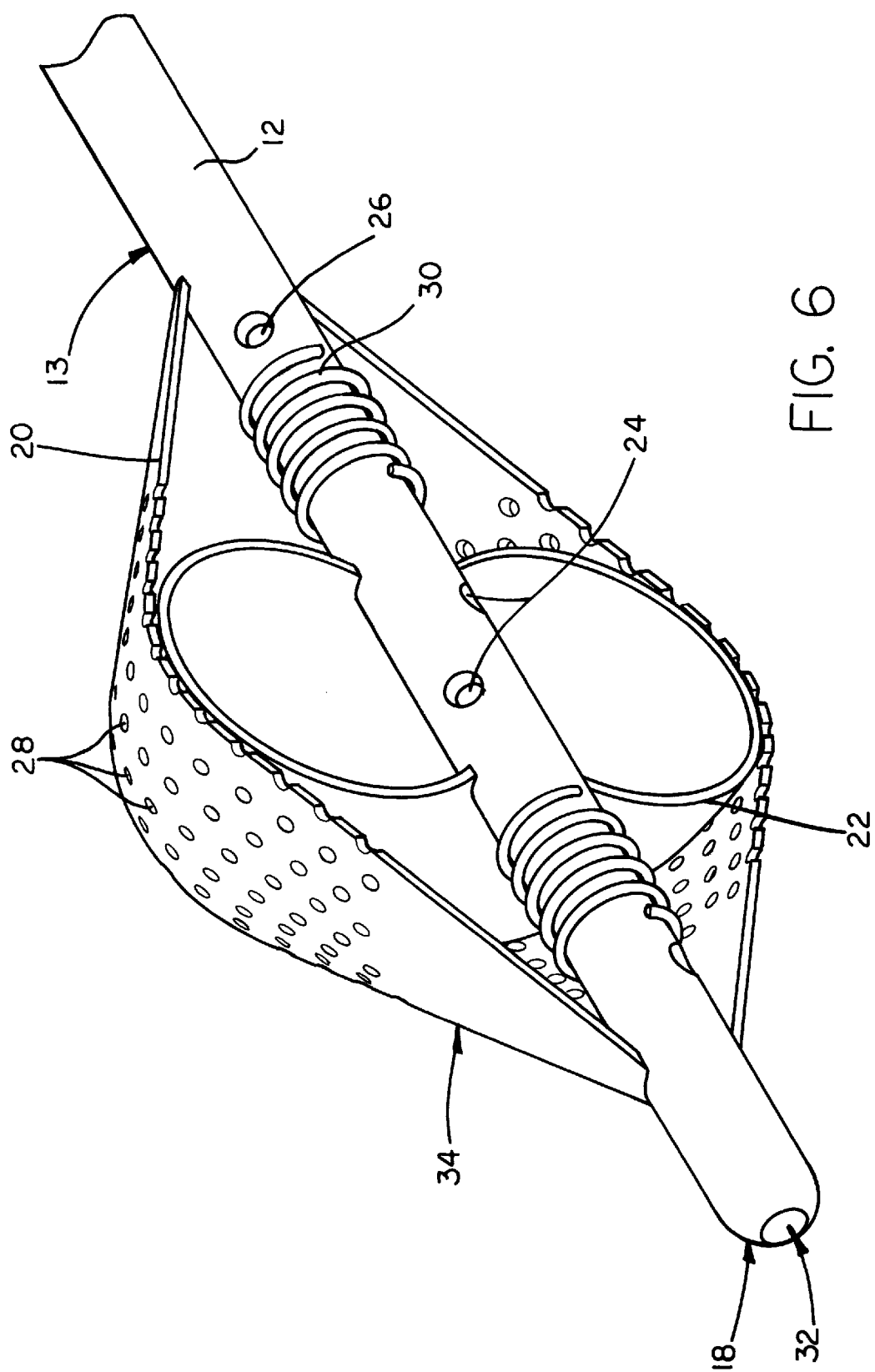
FIG. 6 is a cutaway, perspective view of a distal portion of the ablation catheter of FIG. 5 with the balloons inflated.
Figure 7:
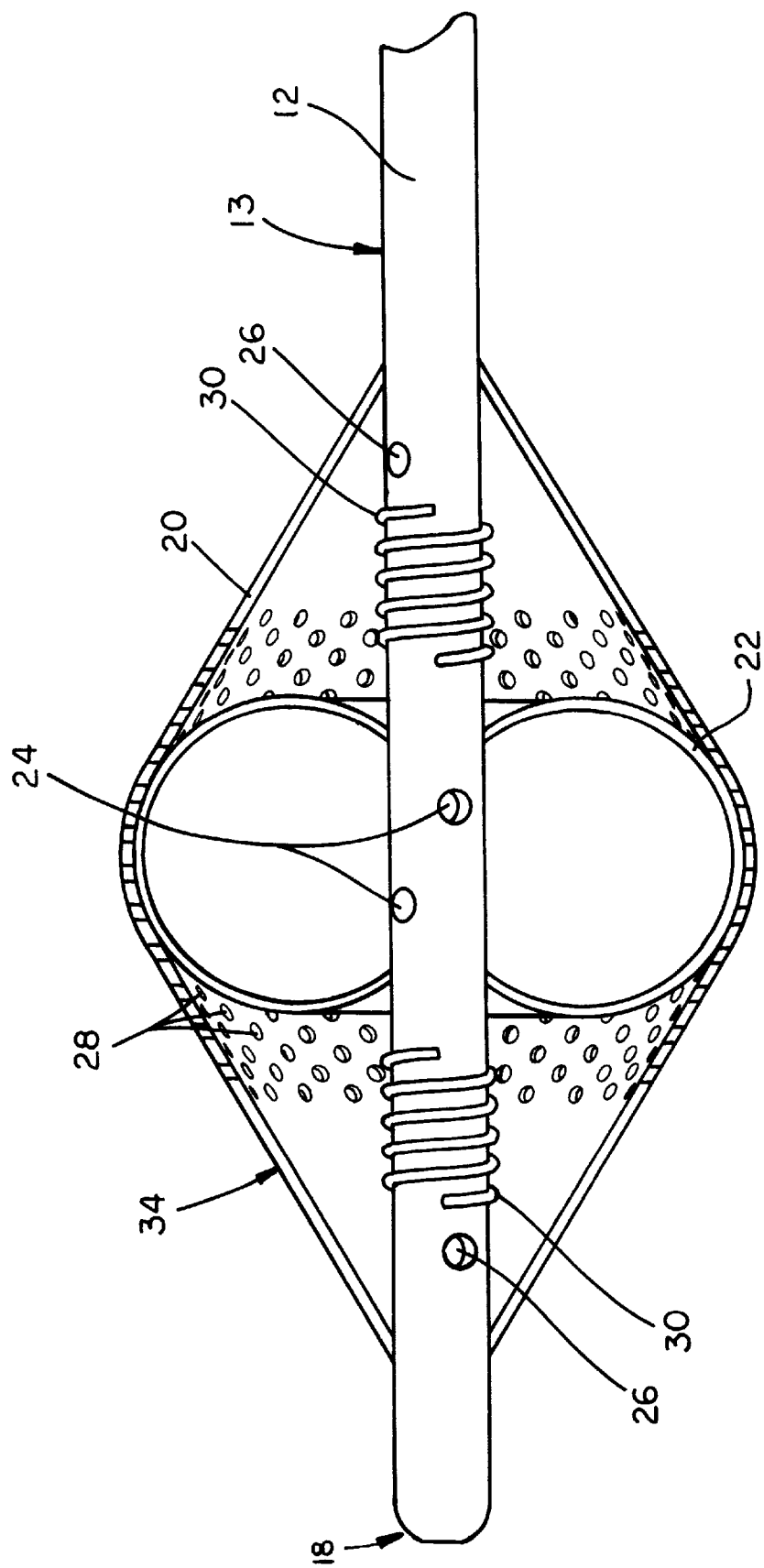
FIG. 7 is a cutaway side view of the distal portion of the ablation catheter of FIG. 5 with the balloons inflated.

The catheter (12) preferably also contains a plurality of conventional lumens which extend from the proximal end (16) of the catheter to or near the distal end (18) of the catheter (12). In one preferred embodiment, the catheter (12) includes at least four separate lumens. The first lumen extends from the proximal end (16) to the distal end (18) of the catheter (12) and ends in a distal opening (32) in the distal end (18) of the catheter (12). This lumen is designed to accommodate a guidewire that passes through the catheter (12) during introduction of the catheter (12) into the pulmonary vein (14). This lumen may also be used for the introduction of a contrast media into the pulmonary vein (14) at a location distal from the balloons (20, 22) of the catheter (12) during the ablation procedure. A second lumen in the catheter (12) receives electrode conductor wires which pass from the proximal end (16) of the catheter to an electrode (30) or electrodes located near the distal end (18) of the catheter (12). The third lumen is designed for introduction of a conductive media into the second, inner balloon (22). This media is utilized to inflate the second, inner balloon (22). For the introduction of media at this location, openings (24) are provided in the catheter (12) at a location within the second, inner balloon (22) as shown in FIGS. 6 and 7. The fourth lumen is designed for the introduction of a conductive media, preferably a saline solution, into the first, outer balloon (20). Media introduction openings (26) are provided in the catheter (12), preferably both proximal and distal from the second inner balloon (22), but inside the first balloon (20) as shown in FIGS. 6 and 7 to receive this conductive media. This conductive media is designed to conduct energy from the electrodes (30) secured to the catheter (12) through the balloon openings (28) in the surface (34) of the outer balloon (22) to contact the inner surface of the pulmonary veins (14). Additional lumens may be provided in the catheter (12) for other conventional utilizations.

The invention also includes an introducing system to introduce conductive media into the space within the first, outer balloon (20), and an ablating system secured to the outside surface (13) of the catheter (12) at a location within the first balloon (20), but outside of the second balloon (22). Other components may also be secured to the catheter (12) to assist in the formation of circumferential ablation lesions, including, for example sensors (not shown) to sense the presence of premature atrial contractions, temperature sensors (not shown) to sense the temperature of the tissue being ablated, markers (not shown) to mark the location of the catheter (12) and its components within the pulmonary vein (14) and other conventional components normally utilized with an ablation catheter (12).

The two balloons (20, 22) are secured to the outer surface (13) of the catheter (12) as shown in FIGS. 3–8. The first, outer balloon (20) typically measures from about 10 mm (0.4 in.) to about 100 mm (4.0 in.) in length and when inflated generally conforms to an ellipsoid shape as shown in FIGS. 5, 6 and 7. The maximum diameter of the first, outer balloon (20) when fully inflated is variable up to about 60 mm (2.4 in.). The second, inner balloon (22) is also secured to the outer surface (13) of the catheter (12) at a location within the first, outer balloon (20) as shown in FIGS. 5, 6 and 7. When inflated, the second, inner balloon (22) measures approximately 2 mm (0.1 in.) to about 100 mm (4.0 in.) in length, preferably 5 mm (0.2 in.) to about 20 mm (0.8 in.), with approximately the same diameter as the first outer balloon (20). Preferably, inflation of the second, inner balloon (22) also inflates the first, outer balloon (20) and maintains the outer balloon (20) in that inflated position throughout the ablation procedure as shown in FIGS. 5, 6 and 7.

The balloons (20, 22) are manufactured according to conventional technology from materials such as a flexible or thermoplastic rubber, urethane, latex, cellulose or other conventional materials and are secured to the catheter (12) conventionally.

Inflation of the balloons (20, 22) is accomplished using conventional methods, preferably using a radiopaque contrast solution, and more preferably a marked saline solution. In addition, if desired, radiopaque marker bands (not shown) may be secured to the surface (34) of the first, outer balloon (20) to mark its relative position in the pulmonary vein (14). Once the proper location in the pulmonary vein (14), or the os of the pulmonary vein, is determined, the catheter (12) may be withdrawn slightly from that location so that the subsequently formed circumferential ablation lesion will be located proximal from the source of the premature atrial contraction.

The balloons (20, 22) when properly inflated should prevent completely the flow of blood through the pulmonary vein (14) around the balloons (20, 22). The balloons (20, 22) are preferably inflated by introduction of media through openings (24) within second, inner balloon (22) which inflates both the inner balloon (22) and the outer balloon (20). Alternatively, or additionally, additional media may be introduced through the media introduction openings (26) in the catheter (12) inside the outer balloon (20) to assist in its inflation. In order to assure that the balloons (20, 22) form a tight seal in the pulmonary vein (14), a contrast media may be injected through the distal opening (32) located in the distal tip (18) of the catheter (12). If any leaks are discovered, additional media may be introduced into the inner balloon (22) until the balloons (20, 22) completely stop the flow of blood in the pulmonary vein (14).

Once the balloons (20, 22) are properly inflated, conductive media is introduced into the outer balloon (22) through the media introduction openings (26) in the outer surface (13) of the catheter (12) located proximal and distal from the second, inner balloon (22). Preferably, two such media introduction openings (26) are provided in the catheter (12), both proximal and distal from the second, inner balloon (22) as shown in FIGS. 6 and 7. In one embodiment, the conductive media is a saline solution marked with markers so that it can be monitored by fluoroscopy, although any appropriate conductive media may be used.

Balloon openings (28) are provided in the surface (34) of the first, outer balloon (20) as shown, for example, in FIGS. 6 and 7. In a preferred embodiment, these balloon openings (28) are formed in a series of lines passing around the surface (34) of the first, outer balloon (20). These balloon openings (28) may be formed in a single line, or in a preferred embodiment, they form two or more lines, each running completely around the surface (34) of the first, outer balloon (20) as shown in FIGS. 6 and 7.

Figure 8:
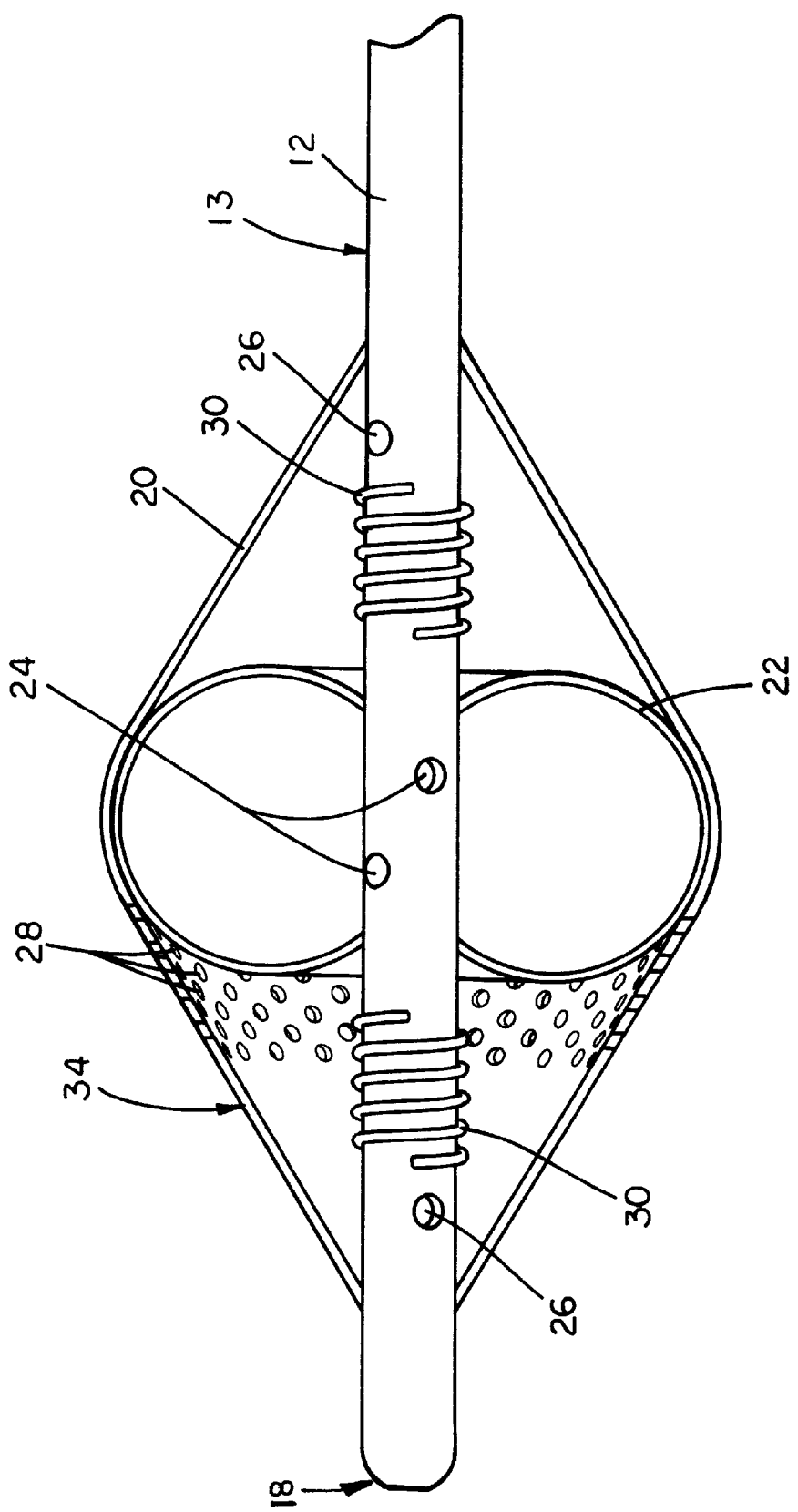
FIG. 8 is a cutaway, side view of the distal portion of the ablation catheter with the balloons inflated, showing an alternative embodiment for the location of the balloon openings in the first, outer balloon.

In an alternative embodiment, these lines of balloon openings (28) are located only distal from the second inner balloon (22) in the first outer balloon (20) as shown in FIG. 8. This alternative structure permits the conductive media to be concentrated distal from the inner balloon (22) within the pulmonary vein (14) against the surface of the tissue and not be dissipated into the left atrium (11).

The electrodes (30), located within the first, outer balloon (20), but outside of the second inner balloon (22), preferably emit radiofrequency energy, which is conducted by the conductive media through the balloon openings (28) in the surface (34) of the first outer balloon (20) to the tissue within the pulmonary vein (14). Because these balloon openings (28) are formed in a line or lines around the surface (34) of the first, outer balloon (20), the conductive energy emitted by the electrodes (30) forms a circumferential lesion inside the pulmonary vein (14).

While the preferred source for the ablation energy is radiofrequency energy, other sources of energy may be utilized, such as microwave, ultrasound or heat. During the ablation process, the energy from the catheter (12) is conducted by the conductive media to the tissue within the pulmonary vein (14). In a preferred embodiment, the impedance of the conductive media should be less than the impedance of the human tissue so that the tissue will heat up to an ablation temperature at a faster rate than does the media.

Figure 9:
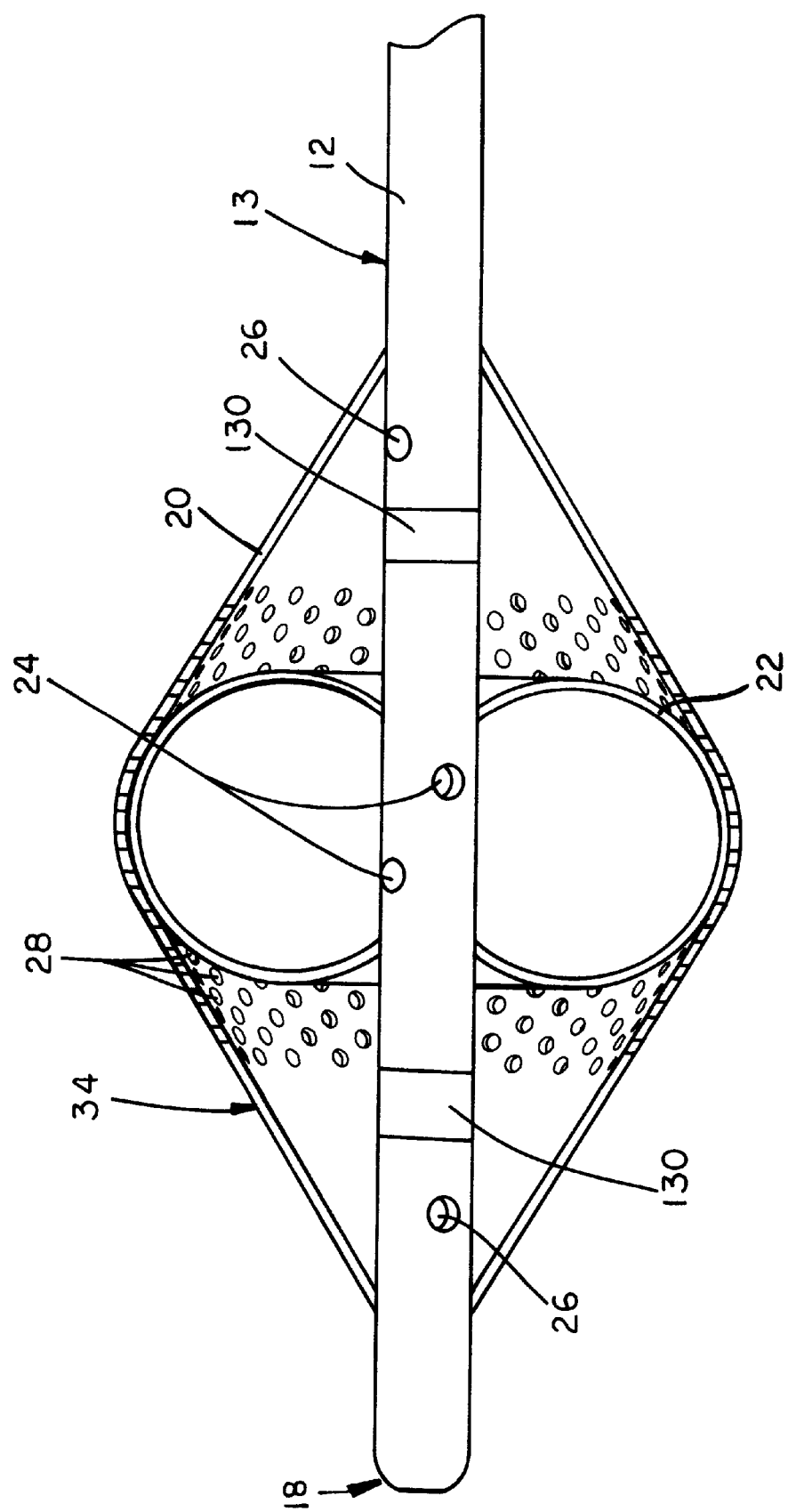
FIG. 9 is a cutaway, perspective view of an alternative embodiment of the ablation catheter of FIG. 7, wherein a ring electrode replaces the coil electrode.
Figure 10:
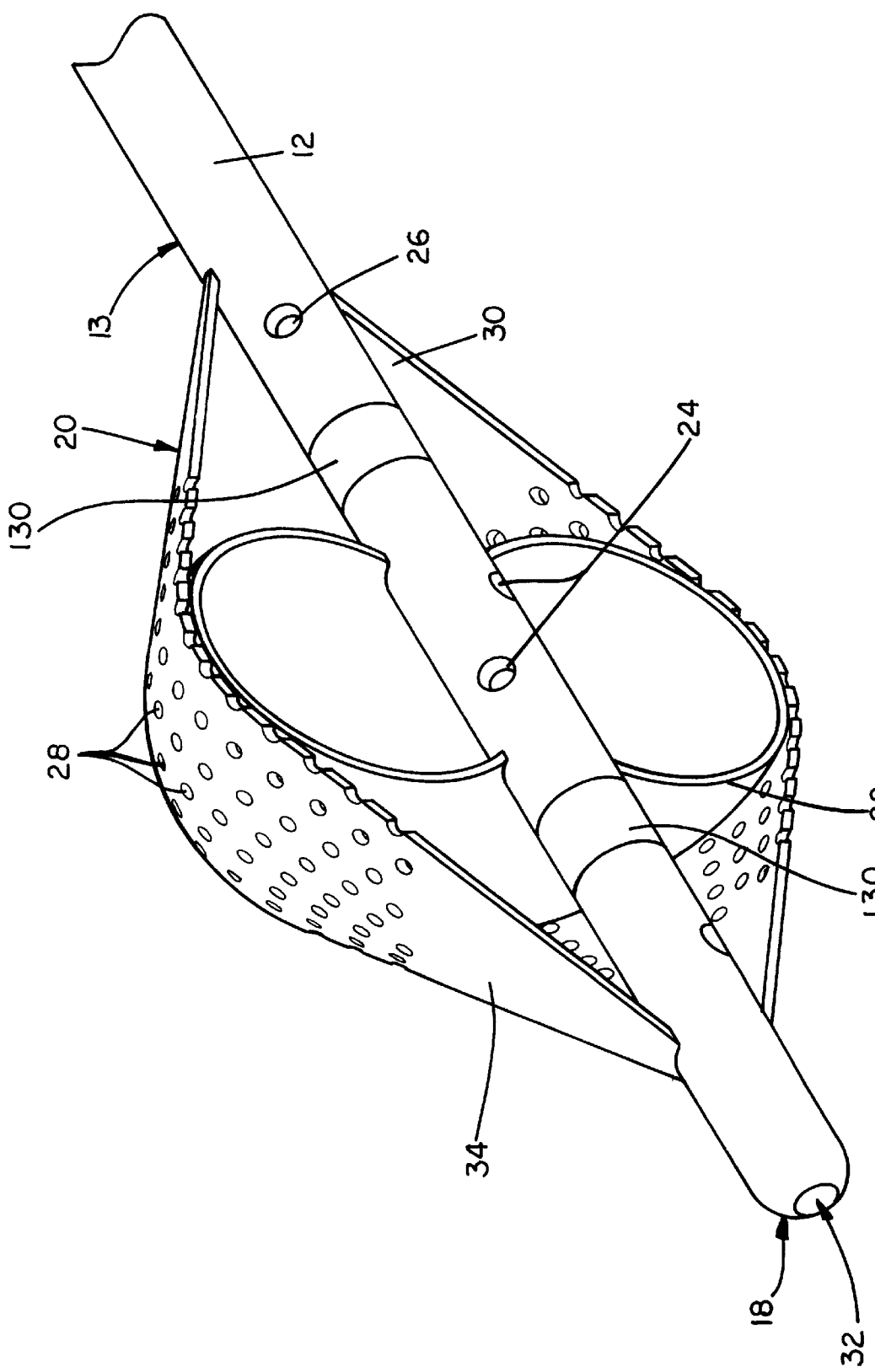
FIG. 10 is a cutaway, side view of the distal portion of the alternative embodiment of the ablation catheter of FIG. 9.

The ablating system can consist of a pair of coil electrodes (30) as shown in FIGS. 6 and 7 or, alternatively, ring electrodes (130) as shown in FIGS. 9 and 10. In a preferred embodiment two electrodes, either coil (30) or ring (130), are secured to the catheter (12), one proximal and one distal from the inner balloon (22), but both inside the outer balloon (20).

In order to monitor the formation of the ablation lesion, a temperature sensor (not shown), such as a thermistor or thermocouple can also be secured to the outer surface (13) of the catheter (12). Sensing electrodes (not shown) can also be secured to the catheter (12) at any appropriate location to monitor electrical activity in the pulmonary vein.

In operation, a modified Seldinger technique is normally used for the insertion of the medical device (10) into the body. Using this procedure, a small skin incision is made at the appropriate location to facilitate catheter or dilator passage. Subcutaneous tissue is then dissected, followed by a puncture of the vessel with an appropriate needle with a stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed, leaving a portion of the guidewire exposed outside of the vessel. The guidewire is then advanced into the right femoral vein and through the inferior vena cava into the right atrium. (The preferred procedure uses the inferior approach to the right and left atria. Procedures for the retrograde and superior approach to the left atrium can also be used and are within the scope of the invention.) With the guidewire in place, a dilator is then passed over the guidewire with an introducer. The dilator and introducer generally form an assembly to be advanced together along the guidewire into the inferior vena cava. The introducer may be a conventional straight introducer or, preferably, a precurved introducer, such as the SL2 introducer sold by Daig Corporation.

A Brockenbrough needle or trocar is then inserted through the lumen of the dilator to the right atrium to be used to create an opening through the interatrial septum, preferably at the fossa ovalis. The entire assembly (dilator, introducer and Brockenbrough needle) passes through the vena cava into the right atrium so that the tip rests against the interatrial septum at the level of the fossa ovalis. The Brockenbrough needle is then advanced through the fossa ovalis. After the opening is made through the interatrial septum, the Brockenbrough needle is exchanged for a guidewire. The dilator, guidewire and guiding introducer for the left atrium are then advanced into the left atrium. The dilator is then removed leaving the introducer and guidewire in place in the left atrium. The ablation catheter (12) is then advanced through the lumen of the introducer over the guidewire and into the left atrium. The guidewire is then maneuvered until it enters the appropriate pulmonary vein (14). The catheter (12) is then advanced over the guidewire into the pulmonary vein and the guidewire is removed.

Once the distal end (16) of the ablation catheter (12) has been advanced into the pulmonary vein (14), it may be positioned by use of a sensing electrode (not shown) secured at or near the distal end (16) of the catheter (12). This sensing tip electrode senses electrical activity within the pulmonary vein (14), including atrial premature contractions. Once the source of the atrial premature contractions has been confirmed to be distal to the inner balloon (22) and outer balloon (20), the inner balloon (22) is inflated by introducing media through the media introduction openings (26) in the catheter (12). By inflating the inner balloon (22), the outer balloon (20) is also inflated. This inner balloon (22) and outer balloon (20) must be sufficiently inflated to prevent completely the flow of blood through the pulmonary vein (14) around the balloons (20, 22). To assure that no blood flows around the balloons (20, 22), marked media may be injected into the pulmonary vein (14) at a point distal from the balloons (20, 22), for example, through the opening (32) in the distal tip (18) of the catheter (12). Any leakage around the balloons (20, 22) can then be determined by fluoroscopy and eliminated by additional pressure on the inside of the inner balloon (22).

The ablating system, preferably a pair of Rf coil electrodes (30), or ring electrodes (130), which are secured to the outer surface (13) of the catheter (12) at a location within the outer balloon (20) and outside of the inflated inner balloon (22), then emit energy which is conducted by the conductive media through the balloon openings (28) in the surface (34) of the outer balloon (20) to the surface of the tissue in the pulmonary vein (14). Sufficient energy is emitted to create a circumferential lesion of sufficient width and depth to block completely the passage of the atrial premature contractions through the pulmonary vein (14). The temperature of the tissue of the pulmonary vein (14) may be monitored by temperature sensors, such as thermistors or thermocouples (not shown), located on the surface (13) of the catheter (12) outside the balloons (20, 22). In addition, sensing electrodes (not shown) may be located proximal from the balloons (20, 22) to sense electrical activity through the vessel after the ablation procedure has been completed to assure complete blockage of the pulmonary vein (14). The tissue to be ablated may be at any location within the pulmonary vein (14) or in the os of the pulmonary vein (14).

After the ablation procedure has been completed and tested by use of sensing electrodes, each of the elements of the system are removed from the pulmonary vein (14) and left atrium (11). If desired, additional sensing devices can be introduced into the left atrium (11) to determine whether there are any other sources for the atrial premature contractions in other pulmonary veins (14).

It will be apparent from the foregoing that while particular forms of the invention have been illustrated and described, various modifications can be made without departing from the spirit and scope of the invention. For example, the present invention could also be used for ablation procedures in other vessels such as the coronary sinus and other veins.

We claim:

1. A medical device for ablation within a vessel associated with a human heart comprising
   an ablation catheter,
   a first, outer balloon, secured to the catheter to seal the vessel and substantially prevent the flow of blood through the vessel,
   a second, inner balloon, secured to the catheter at a location within the first outer balloon,
   an introduction system secured to the catheter to introduce a conductive media inside the first outer balloon,
   an ablating element secured to the catheter within the first outer balloon, and
   a plurality of balloon openings provided in an outside surface of the first, outer balloon.

2. The medical device of claim 1 wherein the ablating element comprises a ring electrode.

3. The medical device of claim 1 wherein the ablating element comprises a coil electrode.

4. The medical device of claim 1 wherein the introduction system comprises a lumen which extends through the catheter into a media introduction opening in the catheter located within the first outer balloon.

5. The medical device of claim 1 wherein the balloon openings extend around a circumference of the first, outer balloon.

6. The medical device of claim 5 wherein the balloon openings are located on a distal portion of the first, outer balloon.

7. The medical device of claim 2 wherein the ring electrode is secured to the catheter at a location within the outer balloon but outside of the inner balloon.

8. The medical device of claim 3 wherein the coil electrode is secured to the catheter at a location within the outer balloon but outside of the inner balloon.

9. The medical device of claim 1 further comprising a lumen in the catheter including a distal opening in the catheter, which distal opening is located distal from the first and second balloons.

10. The medical device of claim 2 wherein the ring electrode emits radiofrequency energy.

11. The medical device of claim 3 wherein the coil electrode emits radiofrequency energy.

12. The medical device of claim 1 wherein the conductive media is a conductive saline solution.

13. A medical device for ablation within a vessel associated with a human heart comprising
   an introducer with a proximal and a distal end and a lumen passing through the introducer from its proximal to its distal end,
   an ablation catheter inserted within the lumen of the introducer,
   a first, outer balloon, secured to the catheter to seal the vessel and substantially prevent the flow of blood through the vessel,
   a second, inner balloon, secured to the catheter at a location within the first outer balloon,
   an introduction system secured to the catheter within the first outer balloon,
   an ablating element secured to the catheter located within the first outer balloon, and
   a plurality of balloon openings provided in an outside surface of the first outer balloon.

14. The medical device of claim 13 wherein the ablating element comprises a ring electrode.

15. The medical device of claim 13 wherein the ablating element comprises a coil electrode.

16. The medical device of claim 13 wherein the plurality of balloon openings are provided in a line in the outside surface of the first outer balloon.

17. The medical device of claim 16 wherein the balloon openings extend around a circumference of the first, outer balloon.

18. The medical device of claim 16 wherein the balloon openings are located on a distal portion of the first, outer balloon.

19. The medical device of claim 14 wherein the ring electrode is secured to the catheter at a location within the outer balloon but outside of the inner balloon.

20. The medical device of claim 15 wherein the coil electrode is secured to the catheter at a location within the outer balloon but outside of the inner balloon.

21. A process for ablation of tissue within a vessel of a human comprising introducing an ablation catheter into the vessel, wherein the ablation catheter comprises an extended catheter, a first, outer balloon, secured to the catheter, and a second inner balloon, secured to the catheter and located inside the first outer balloon, sealing the vessel to prevent substantially the flow of blood through the vessel by use of the first outer balloon, introducing a conductive media within the first outer balloon through a lumen in the catheter, passing the conductive media through balloon openings in an outside surface of the first outer balloon, conducting energy from an electrode secured to the catheter by use of the conductive media through the balloon openings in the outer balloon to the tissue, and ablating the tissue to form a circumferential ablation lesion.

22. The medical device of claim 1 wherein the ablating element comprises an electrode, and wherein the electrode is secured to the ablation catheter at a location within the outer balloon, but outside of inner balloon.

* * * * *